United States Patent
Wang et al.

(10) Patent No.: US 9,014,423 B2
(45) Date of Patent: Apr. 21, 2015

(54) METHOD AND SYSTEM FOR CATHETER TRACKING IN FLUOROSCOPIC IMAGES USING ADAPTIVE DISCRIMINANT LEARNING AND MEASUREMENT FUSION

(75) Inventors: Peng Wang, Princeton, NJ (US); Yefeng Zheng, Dayton, NJ (US); Matthias John, Nürnberg (DE); Jan Boese, Eckental (DE); Gareth Funka-Lea, Cranbury, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 544 days.

(21) Appl. No.: 13/412,882

(22) Filed: Mar. 6, 2012

(65) Prior Publication Data
US 2012/0238866 A1 Sep. 20, 2012

Related U.S. Application Data

(60) Provisional application No. 61/452,263, filed on Mar. 14, 2011, provisional application No. 61/505,131, filed on Jul. 7, 2011.

(51) Int. Cl.
*G06K 9/00* (2006.01)
*A61B 6/00* (2006.01)
*A61B 6/12* (2006.01)
*G06T 7/20* (2006.01)

(52) U.S. Cl.
CPC . *A61B 6/487* (2013.01); *A61B 6/12* (2013.01); *A61B 6/503* (2013.01); *G06T 7/2033* (2013.01); *G06T 2207/10016* (2013.01); *G06T 2207/10064* (2013.01); *G06T 2207/20076* (2013.01); *G06T 2207/20081* (2013.01); *G06T 2207/30021* (2013.01); *G06T 2207/30048* (2013.01)

(58) Field of Classification Search
None
See application file for complete search history.

(56) References Cited

U.S. PATENT DOCUMENTS 6,961,608 B2 11/2005 Hoshino et al.
7,920,911 B2 4/2011 Hoshino et al.
(Continued)

FOREIGN PATENT DOCUMENTS

CN 101221620 A 7/2008
CN 101371784 A1 2/2009
(Continued)

OTHER PUBLICATIONS

Wang et al. "Robust guidewire tracking in fluoroscopy," Computer Vision and Pattern Recognition, Jun. 20-25, 2009. CVPR 2009. IEEE Conference on , pp. 691-698.*
Collins, et al. "Online selection of discriminative tracking features," 2005, IEEE Trans. on PAMI 27(10), 1631-1643.*
(Continued)

*Primary Examiner* — Matthew Bella
*Assistant Examiner* — Jason Heidemann

(57) ABSTRACT

A method and system for adaptive discriminant learning and measurement fusion for image based catheter tracking is disclosed. An adaptive discriminant model is trained online based on a tracked object, such as a pigtail catheter tip, in at least one previous frame of a fluoroscopic image sequence. The object is tracked in the current frame of the fluoroscopic image sequence based at least on the adaptive discriminant model trained online. The object may be tracked in the current frame based on a fusion of three types of measurement models including the adaptive discriminant model trained online, an object detection model trained offline, and an online appearance model.

26 Claims, 8 Drawing Sheets

(56) References Cited

U.S. PATENT DOCUMENTS

| | | | |
|---|---|---|---|
| 2002/0085681 A1 | 7/2002 | Jensen | |
| 2005/0245814 A1* | 11/2005 | Anderson et al. | 600/410 |
| 2008/0033452 A1* | 2/2008 | Vetter et al. | 606/130 |
| 2009/0062641 A1 | 3/2009 | Barbu et al. | |
| 2010/0157041 A1* | 6/2010 | Klaiman et al. | 348/77 |
| 2010/0222671 A1* | 9/2010 | Cohen et al. | 600/424 |
| 2010/0228076 A1* | 9/2010 | Blank et al. | 600/18 |
| 2010/0239148 A1 | 9/2010 | Zheng et al. | |
| 2010/0249579 A1 | 9/2010 | Starks | |
| 2010/0290693 A1* | 11/2010 | Cohen et al. | 382/134 |
| 2011/0038517 A1 | 2/2011 | Strother | |
| 2011/0164035 A1 | 7/2011 | Liao et al. | |
| 2012/0004533 A1* | 1/2012 | Peng et al. | 600/424 |

FOREIGN PATENT DOCUMENTS

| | | |
|---|---|---|
| CN | 101661559 A | 3/2010 |
| CN | 101908153 A | 12/2010 |
| WO | 03041057 A3 | 2/2004 |

OTHER PUBLICATIONS

Lin et al. "Object Tracking Using Incremental Fisher Discriminant Analysis," (2004), In: ICPR, vol. 2, pp. 757-760.*

Wang et al. "Hierarchical Guidewire Tracking in Fluoroscopic Sequences", Mar. 27, 2009, Proc. SPIE 7259, Medical Imaging 2009: Image Processing, pp. 1-8.*

Chinese Office Action dated Sep. 1, 2014 Application No. 201210120135.2.

* cited by examiner

FIG. 4
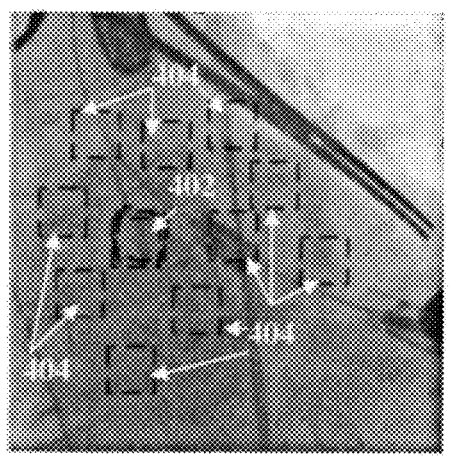
(a)
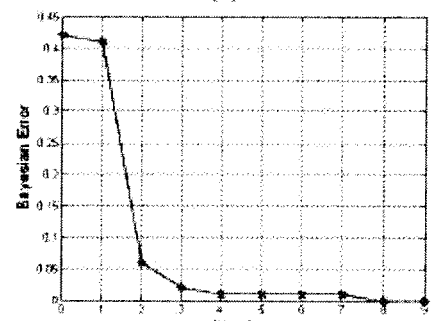
(b)

FIG. 6

600 {
- Train an initial discriminant vector $A^{(0)}$
  602 ▸ 1. Train PCA and then FDA from training samples, and obtain $A^{(0)}$;
  604 ▸ 2. Learn a probabilistic model of linear discriminant analysis, as Eqn. (5);

610 {
- Adaptive learning during tracking
  3. Add positive samples from tracked objects (or from tracking initialization at the first frame), and
  612 ▸ generate the negative samples way from tracked objects;
  4. Repeat the steps a)-c) until the learning converges or $C(A)$ is less than a threshold (e.g., 0.1):
  614 ▸ a). Update the discriminant vector A based on Eqn. (8) and (7);
  616 ▸ b). Update the probabilistic model, as Eqn. (5);
  618 ▸ c). Compute the Bayesian error $C(A)$ as Eqn. (6);
  5. If the learning converges, update the discriminant analysis and save the tracked objects into positive
  620 ▸ samples.

METHOD AND SYSTEM FOR CATHETER TRACKING IN FLUOROSCOPIC IMAGES USING ADAPTIVE DISCRIMINANT LEARNING AND MEASUREMENT FUSION

This application claims the benefit of U.S. Provisional Application No. 61/452,263, filed Mar. 14, 2011, and U.S. Provisional Application No. 61/505,131, filed Jul. 7, 2011, the disclosures of which are herein incorporated by reference.

BACKGROUND OF THE INVENTION

The present invention relates to medical imaging, and more particularly, to automatic tracking of catheter motion in a fluoroscopic image sequence.

Aortic valve disease affects a large number of people globally and is the most common type of valvular disease in developed countries. Implantation of a prosthetic aortic valve is often necessary to replace a severely damaged native valve. Although open-chest valve surgery is a well established procedure, minimally invasive transcatheter aortic valve implantation (TAVI) is an emerging technique, especially for high-risk patients, to minimize the surgical trauma. Interventional surgeries, such as TAVI, are typically performed under the guidance of real time fluoroscopic (x-ray) images. As the minimally invasive TAVI technique is emerging, physicians increasingly focus on minimizing the risks and making the surgery lass invasive in order to minimize the trauma, especially for high-risk patients. For example, it is desirable to reduce the times of exposure to and the amount of the potentially toxic contrast agent that is injected into a patient's blood. Most of such contrast in used to highlight the aorta and coronaries in fluoroscopic images in order to visually guide physicians. For example, when contrast is injected in TAVI, the aorta will be visible and an annulus line can be identified in a 2D fluoroscopic image. When there is no contrast injection, the aorta and annulus line will not be visible. Accordingly, it is desirable to track the motion of the aorta in non-contrast enhanced fluoroscopic images in order to reduce the exposure of patients to the contrast agent.

BRIEF SUMMARY OF THE INVENTION

The present invention provides a method and system for automatically tracking an object, such as a catheter, in a sequence of fluoroscopic images. Embodiments of the present invention utilize adaptive discriminant learning and measurement fusion for image-based catheter tracking. Embodiments of the present invention can be used to track a pigtail catheter in trans-catheter aortic valve implantation (TAVI). Since the pigtail catheter has the same motion as the aorta, it is possible to track the motion of the aorta by tracking the pigtail catheter.

In one embodiment of the present invention, an adaptive discriminant model is trained online based on a tracked object, such as a pigtail catheter tip, in at least one previous frame of a fluoroscopic image sequence. The object is tracked in the current frame of the fluoroscopic image sequence based at least on the adaptive discriminant model trained online. The object may be tracked in the current frame based on a fusion of three types of measurement models including the adaptive discriminant model trained online, an object detection model trained offline, and an online appearance model.

These and other advantages of the invention will be apparent to those of ordinary skill in the art by reference to the following detailed description and the accompanying drawings.

BRIEF DESCRIPTION OF THE DRAWINGS

FIG. 4 illustrates an example of adaptive discriminant learning for detection of a pigtail catheter in a fluoroscopic image sequence;

FIG. 6 illustrates an algorithm for performing the adaptive discriminant learning according to an embodiment of the present invention;

DETAILED DESCRIPTION

The present invention is directed to a method and system for automatically tracking an object, such as a catheter, in a fluoroscopic image sequence. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Figure 1:
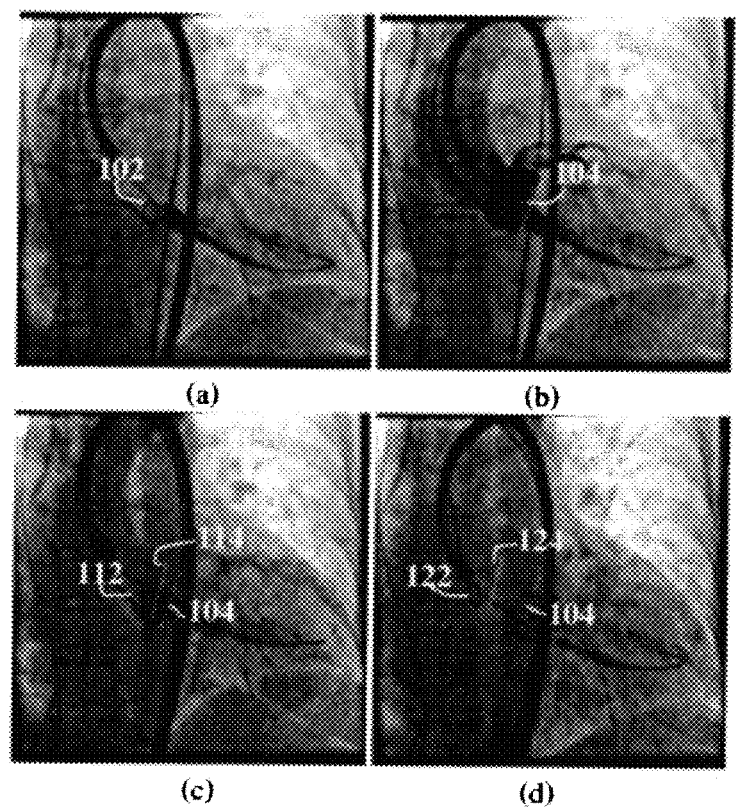
FIG. 1 illustrates an example of motion compensation for aortic valve implantation by tracking a pigtail catheter.

Embodiments of the present invention provide a computational framework for robustly tracking an object by adaptive discriminant learning and measurement fusion. Such a tracking framework can be applied in Trans-catheter Aortic Valve Implantation (TAVI) in order to track a pigtail catheter. A medical device, such as a pigtail catheter can be tracked in a TAVI procedure to provide motion compensation for a 2D/3D overlay and reduce the exposure of a patient to contrast agent. FIG. 1 illustrates an example of motion compensation for aortic valve implantation by tracking a pigtail catheter. A pigtail catheter is a type of medical device that is inserted into the aorta for cardiac surgical guidance. Embodiments of the present invention track motion the tip of a pigtail catheter, which is the loose circle at the distal end of the pigtail catheter. Image (a) of FIG. 1 shows a pigtail catheter tip 102 detected in a frame of a fluoroscopic image sequence.

When a contrast agent is injected, the aorta and aortic valve will be visible for short period of time, an annulus line can be identified in a 2D fluoroscopic image for visual guidance of the TAVI procedure. Image (b) of FIG. 1 shows an annulus line 104 identified in a 2D fluoroscopic image when contrast in injected. When there is no contrast injection, aorta and aortic valve, and thus the annulus line, will not be visible. During the intervention, the pigtail catheter is continuously tracked in the 2D fluoroscopic images. Under the condition that the pigtail catheter moves with the same motion as the aorta, i.e., the pigtail catheter is not pulled during the intervention, the tracking of the pigtail catheter will provide motion compensation for continuous visualization of the annulus line. Images (c) and (d) respectively show tracked pigtail catheter tip locations 112 and 122 in two frames of a fluoroscopic image sequence, the location of the annulus line 104 identified when contrast was injected, motion-compensated annulus lines 114 and 124 determine based on the tracked pigtail catheter tip locations 112 and 122, respectively. Accordingly, the catheter tracking can provide visual guidance for the aortic valve implantation, and also greatly reduce the amount of contrast agent used during interventions. Although the annulus lines are used as examples, the present invention is not limited thereto. It is also possible that other geometric models, for example the aorta model, are used to visualize the motion compensation.

Figure 2:
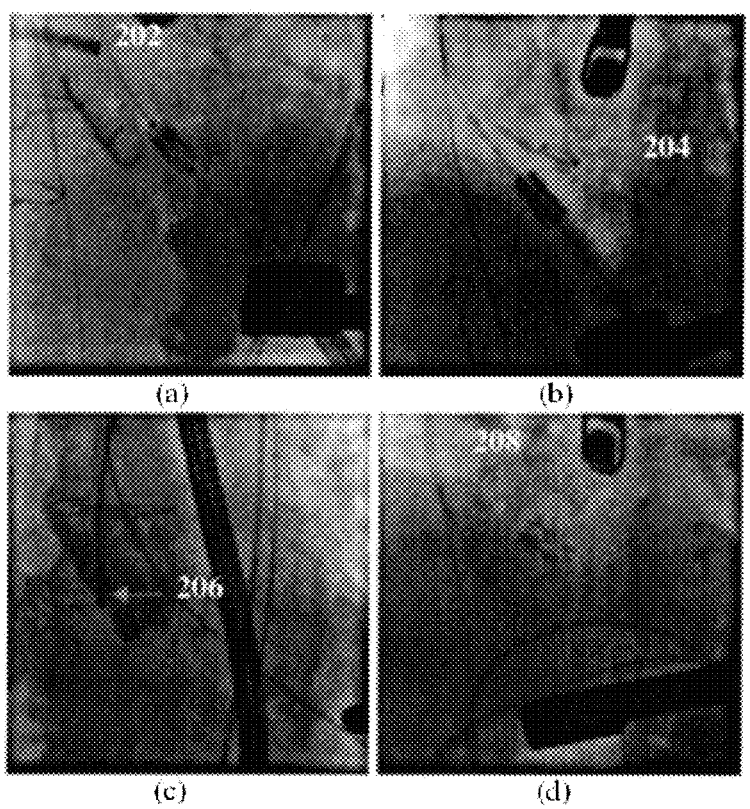
FIG. 2 illustrates examples of pigtail catheters in different fluoroscopic image sequences.

The dynamic clinical environment of the aortic valve implantation presents significant real-world problems for object tracking. For example, when x-ray (fluoroscopic) images are acquired at arbitrary angles, a catheter can appear as a circle, an ellipse, or even a straight line, depending on the projection angle. FIG. 2 illustrates examples of pigtail catheters in different fluoroscopic image sequences. Image (a) shows a fluoroscopic image in which a pigtail catheter tip 202 that appears as a circle. Image (b) shows a fluoroscopic images in which a pigtail catheter tip 204 that appears as an ellipse. Image (c) shows a fluoroscopic image in which a pigtail catheter tip 206 appears as a straight line. Image (d) shows a fluoroscopic image in which a pigtail catheter tip 208 is barely visible due to a low dose radiation x-ray and motion blurring.

Figure 3:
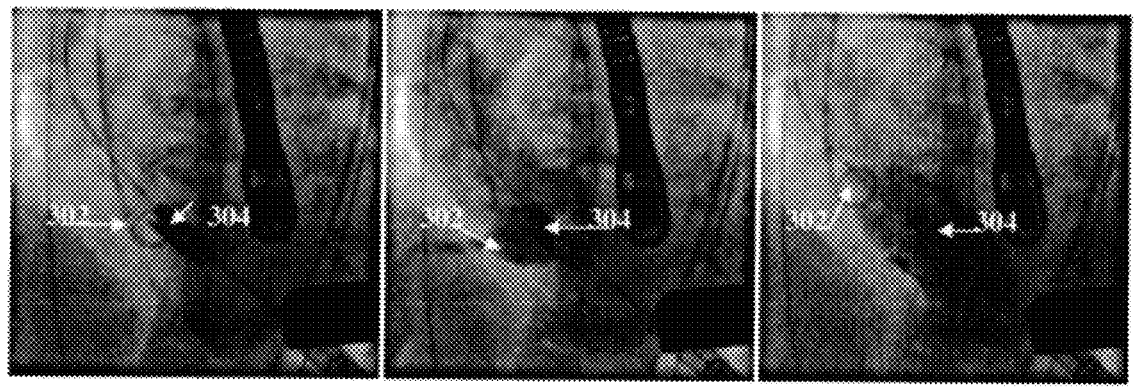
FIG. 3 illustrates a sequence of fluoroscopic images in which a pigtail catheter is occluded by another device.

A pigtail catheter also continuously moves with breathing motion and cardiac motion during image acquisition. As a result of these motions, a catheter could undergo rotation and twisting, and its shape and appearance can change within a fluoroscopic image sequence. Furthermore, when x-ray images are acquired during cardiac interventions, contrast agent is frequently injected in vessels in order to visualize the aorta, and a catheter may be occluded by the injected contrast agent. Moreover, in addition to the pigtail catheter, other devices, such as other catheters, stents, and probes, and anatomic structures, such as ribs and spines, may appear in the x-ray images. Some of the other devices and anatomical structures may be close to or even overlap with the pigtail catheter, which can cause automatic tracking of the pigtail catheter to fail. Because a low dose of radiation is preferred, x-ray images usually have a low signal-to-noise ratio, which can result in the catheter appearing blurry in an x-ray image, such as in image (d) of FIG. 2. FIG. 3 illustrates a sequence of fluoroscopic images in which a pigtail catheter is occluded by another device. As shown in FIG. 3, in a sequence of fluoroscopic images with contrast injection, the pigtail catheter tip 302 is occluded by a stent 304.

In order to address the above described difficulties in such dynamic environments, embodiments of the present invention exploit rich and dynamic information available in fluoroscopic image sequences. Embodiments of the present invention provide a framework, referred to herein as "discriminant tracking", to obtain robust measurements modules to track a class of objects, e.g., pigtail catheters, in dynamic environments. Embodiments of the present invention utilize an adaptive discriminant learning method to build online measurement models to discriminate objects from background. A closed-form analytical solution is developed to efficiently update a discriminant function directly from online images without updating sample covariance matrices. Embodiments of the present invention further introduce a Bayesian based fusion of multiple measurement models in a single measurement model. According to an advantageous embodiment three types of measurement models are combined, with each model exploiting a different type of information available in the image sequence:

1. An online adaptive discriminant model. The online adaptive discriminant model is adaptively learned for each sequence to separate an object from background;
2. An offline learned object detection model. The object detection model is learned offline from a collected set of training data. The offline learned object detection model can handle large variations within a class of objects and can be generalized to a variety of environments; and
3. An online appearance model. The online appearance model is built specifically for the object to be tracked. It exploits the consistency of the object between successive frames of an image sequence.

The adaptive discriminant learning model utilizes a learning method to train a model to separate objects from backgrounds and can effectively handle dynamic environments that can change from one sequence to another. For clarity of notations, the object class is denoted as the "positive" class represented $\Omega_+$ by and the background is denoted as the "negative" class represented by $\Omega_-$. An observed image is denoted as Z. A data vector extracted from an image patch is denoted as x, and its associated class label is $l_x$. $l_x=1$ indicates that x belongs to the object class, while $l_x=-1$ indicates that x belongs to the background.

In linear discriminant analysis, an original data vector is projected to a subspace of lower dimensionality where objects are more easily separated from the background. The projection is represented by a linear transformation, i.e., $y=\Phi^T x$, where $\Phi$ is the linear transformation matrix (or a vector). In an advantageous implementation, Fisher discriminant analysis (FDA) is used. FDA provides an optimal solution under the assumption that each class can be approximated by a Gaussian class distribution. FDA extracts discriminant features by maximizing the ratio of between-class and within-class variances, as shown in Equation (1):

$$J = \frac{|\Phi^T \Sigma_b \Phi|}{|\Phi^T \Sigma_w \Phi|}, \tag{1}$$

where $\Sigma_b$ and $\Sigma_w$ are between-class and within-class scatter matrices, respectively, calculated as:

$$\Sigma_w = \sum_i \sum_{x \in \Omega_i} P(x)(x - \bar{x}_i)(x - \bar{x}_i)^T \tag{2}$$

$$\Sigma_b = \sum_i P(\Omega_i)(\bar{x}_i - \bar{x})(\bar{x}_i - \bar{x})^T,$$

where $\bar{x}_i$ is the mean vector of the samples from class $\Omega_i$ and $\bar{x}$ is the mean vector of all samples. $P(x)$ and $P(\Omega_i)$ are the prior probabilities of a data vector x and an object $\Omega_i$, respectively. The FDA can be solved as a generalized eigenvector problem:

$$(\Sigma_w^{-1} \Sigma_b)\Phi_k = \lambda_k \Phi_k. \tag{3}$$

The transformation vector $\Phi_k$ is the eigenvector corresponding to the k-th eigenvalue. For the two class problem in object tracking, the rank of $\Sigma_b$ is 1, therefore only one effective eigenvector can be extracted from FDA. The FDA transformation vector is denoted as $A_f$.

In visual tracking, the data vector has high dimensionality. For example, an image data vector has more than 1000 elements for a 40 by 40 image patch, even after removing the corner pixels. The high dimensionality poses challenges to statistical learning as it requires a large amount of training samples. Principal component analysis (PCA) is applied before FDA to reduce data dimensionality. In PCA, each transformation vector $\Psi_k$ corresponds to an eigenvector of a covariance matrix $\Sigma_+ = \Sigma_{x \in \Omega_+}(x-\bar{x}_+)(x-\bar{x}_+)^T$, where $\bar{x}_+$ is the mean of the object class. For the compact representation of the object class, only the first several significant principal components are selected, i.e., $A_p = \lfloor \Psi_1, \ldots, \Psi_n \rfloor$ where n is much smaller than the original data dimension. After the PCA dimensionality reduction, the FDA is applied to principal components instead of the original data. The overall linear discriminant analysis is the combination of PCA and FDA, as shown in Equation (4):

$$y_x = A_f^T A_p^T x = A^T x, \quad (4)$$

where $A = A_p A_f$ is the overall linear discriminant vector.

After learning the linear discriminant vector A, it is straightforward to model the projection of each class as a Gaussian distribution, from which the posterior probability can be estimated. However, according to an advantageous implementation, the sigmoid function may be more suitable to model the posterior probability of two class classifications:

$$P_A(x) = P(l_x = 1 \mid x) = \frac{1}{1 + e^{(ay_x + b)}} = \frac{1}{1 + e^{(aA^T x + b)}}. \quad (5)$$

The parameters a and b can be learned from training samples by regression. Equation (5) provides a probabilistic model of linear discriminant analysis.

The probabilistic linear discriminant can be learned offline from collected training samples. However, the background, and sometimes the object itself, can change from one tracking scenario to another, and may not be seen in the training sets and therefore not be available for offline learning. In dynamic environments, it is advantageous for the discriminant learning to adapt to different tracking scenarios. For this purpose, embodiments of the present invention provide an adaptive discriminant learning method for efficiently and effectively updating the discriminant analysis using online image data.

Most statistical learning algorithms aim at minimization of the Bayesian error, which is equivalent to minimizing the object function C(A) in Equation (6):

$$C(A) = -\left[\sum_{x_i \in \Omega_i} P(x_i) P_A(x_i) - \sum_{x_j \in \Omega_-} P(x_j) P_A(x_j)\right] = \sum_x \frac{-l_x P(x)}{1 + e^{(aA^T x + b)}}. \quad (6)$$

With new online data available during tracking, re-training the probabilistic linear discriminant model may require a large number of training samples and involve re-computation of co-variance metrics and eigenbases. In an advantageous embodiment of the present invention, the probabilistic linear discriminant model is retrained online using a gradient descent method. To minimize the Bayesian error, the discriminant model is iteratively updated as shown in Equations (7):

$$A^{(k)} = A^{(k-1)} - \delta_k \nabla_A C(A^{(k-1)}), \quad (7)$$

Where $\delta_k$ is an updating step at the k-th iteration. The updating is iterated until it converges. The gradient of the object function $\nabla_A C(A)$ is given by:

$$\nabla_A C(A) = \sum_{x_t} \nabla_A \left(\frac{-l_i P(x_i)}{1 + e^{(aA^t x_t + b)}}\right) = \sum_{x_t} l_i P(x_i) \frac{ae^{(aA^t x_t + b)}}{(1 + e^{(aA^t x_t + b)})^2} x_i. \quad (8)$$

After the linear discriminant vector A is updated at each iteration, the parameters a and b are also updated via regression.

Since the adaptive learning is a greedy method, it needs a good starting point to converge to a good solution. The starting point can be the discriminant learned offline from collected training samples, denoted as $A^{(0)}$. Even if the initial discriminant does not fit the current environment, the adaptive learning can quickly converge to a good solution. FIG. 4 illustrates an example of adaptive discriminant learning for detection of a pigtail catheter in a fluoroscopic image sequence. In the example of FIG. 4, the pigtail catheter appears as almost a line and the initial discriminant model has a large error of above 40%. During tracking, A is updated at each frame based on the tracked results (or the initialization at the first frame) as positive samples and image patches away from the tracked objects as negative samples. Image (a) of FIG. 4 shows positive samples 402 and negative samples 404 extracted from a frame of a fluoroscopic image sequence. In a possible implementation, the tracked (or initialized) object can be shifted and rotated to introduce a variation in the positive samples 402. Image (b) of FIG. 4 shows a curve representing the error of the discriminant model during adaptive learning at a frame. As shown in image (b) of FIG. 4, the error of the initial discriminant model begins at above 40% and the greedy searching (i.e., the gradient descent iterations) converges within a few iterations to achieve a Bayesian error of less than 10%. To improve learning robustness, a history of tracked objects from previous frames is kept in the positive pools to make sure the learning is not distracted by tracking errors at individual frames. Furthermore, the Bayesian error as expressed in Equation (6) is used as a criterion to decide if the learning has converged to an optimal solution. This allows the adaptive learned discriminant model to exclude some non-objects from positive samples that may be caused by occlusions or tracking errors.

Figure 5:
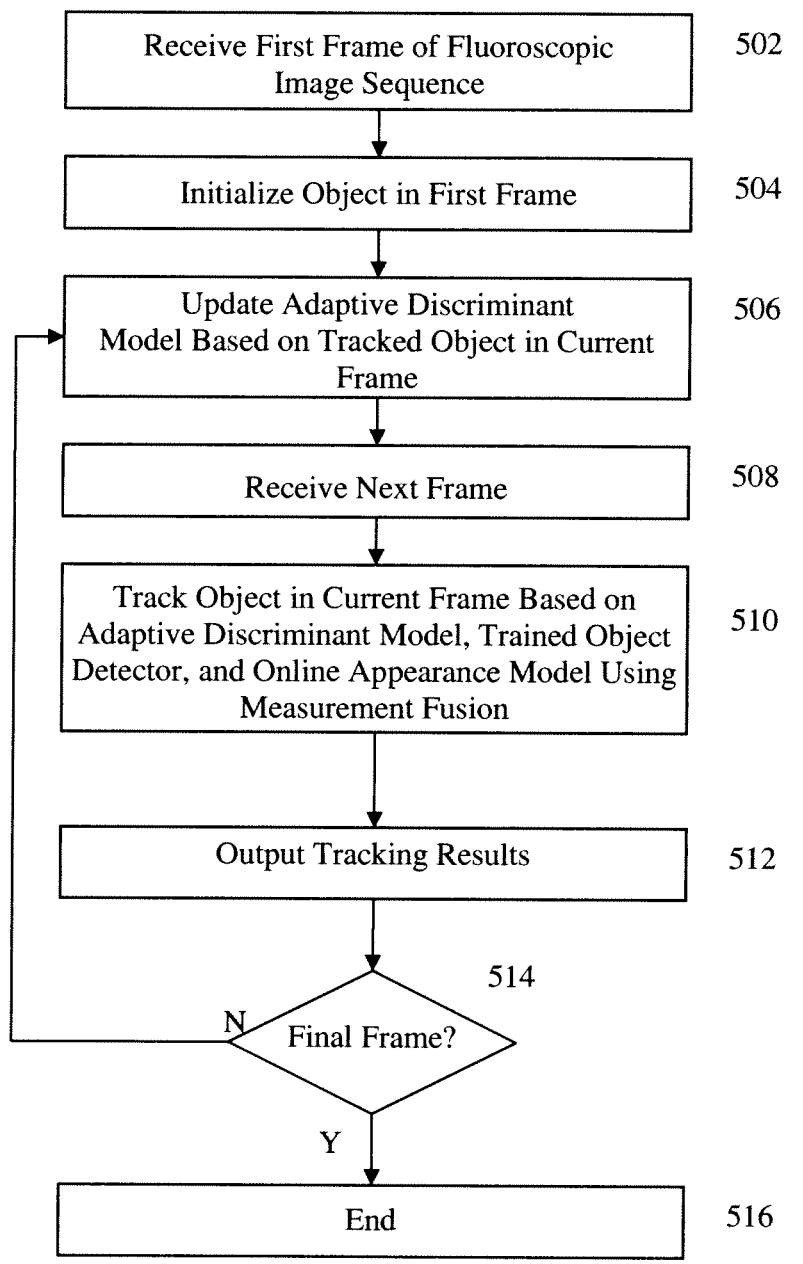
FIG. 5 illustrates a method for tracking an object in a sequence of medical images according to an embodiment of the present invention.

FIG. 5 illustrates a method for tracking an object in a sequence of medical images according to an embodiment of the present invention. In an advantageous embodiment, the method of FIG. 5 may be used to track a pigtail catheter in a sequence of fluoroscopic images in a trans-catheter aortic valve implantation (TAVI). However, the present invention is no limited thereto, and the method of FIG. 5 may be similarly applied for tracking other medical devices as well. The method of FIG. 5 utilizes a Bayesian framework for measurement fusion in object tracking. The method of FIG. 5 integrates three types of measurements for tracking: an adaptively learned discriminant model, an offline learned object detection model, and an online appearance model. The models exploit different types of information, while their fusion makes the overall tracking more robust to dynamic changes of objects in a cluttered environment.

As illustrated in FIG. 5, at step 502, a first frame of a fluoroscopic image sequence is received. For example, the first frame of the fluoroscopic image sequence may be received from an x-ray imaging device as the fluoroscopic image sequence is captured by the x-ray imaging device. It is also possible that the fluoroscopic image sequence is received by loading previously generated fluoroscopic images from a computer readable medium, or memory or storage of a computer system. The fluoroscopic image sequence is a temporal series of frames, in which each frame is a 2D fluoroscopic image. According to an advantageous embodiment, the fluoroscopic image sequence can be received by receiving fluoroscopic images from an x-ray imaging device in real time during an interventional procedure, such as a TAVI procedure.

At step 504, the object is initialized in the first frame of the fluoroscopic image sequence. In one embodiment, the object, e.g., pigtail catheter, may be initialized in a first frame by a user manually annotating the location of the pigtail catheter in the first frame. In an alternative embodiment, the object may be initialized by automatically detecting the object in the first frame of the fluoroscopic image sequence. For example, a pigtail catheter can be automatically detected in a frame of a fluoroscopic image sequence using the method disclosed in U.S. Provisional Application No. 61/505,131, filed Jul. 7, 2011, the disclosure of which is incorporated herein by reference.

At step 506, an adaptive discriminant model is updated based on the tracked object in the current frame. In particular, online adaptive learning is applied to the discriminant model in order to update the discriminant model based on the tracked object in the current frame or the initialized object in the first frame. In the first frame, an initial discriminant vector, which is learned offline from annotated training data, is updated based on the initialized object. FIG. 6 illustrates an algorithm for performing the adaptive discriminant learning according to an embodiment of the present invention. As illustrated in FIG. 6, a first stage 600 of the algorithm is performed offline to train an initial discriminant vector $A^{(0)}$ and a second stage 610 of the algorithm is performed for each frame of the fluoroscopic image sequence to use adaptive learning to update the discriminant vector A and corresponding probabilistic model based on the tracked object in each frame. In the first stage 600, which is performed offline, at 602, the PCA and FDA are trained from training samples. The training samples are extracted from training data that is annotated with ground truth object locations. In particular, PCA is applied to reduce the dimensionality of the data, and after the PCA dimensionality reduction, the FDA is applied to the principal components in order to train a linear discriminant vector as shown in Equation (4) above. At 604, a probabilistic model of the linear discriminant analysis is learned, as shown in Equation (5). The parameters of the probabilistic model can be learned from the training samples using regression.

The second stage 610 of the algorithm of FIG. 6 is performed online during object tracking for each frame of the image sequence. In an advantageous implementation, the second stage 610 of the algorithm of FIG. 6 is used to implement step 506 of the method of FIG. 5. At 612, positive samples corresponding to the tracked object in the current (or initialized object in the first frame) and negative samples away from the object are generated. In particular, the image patch containing the tracked object in the current frame is added as a positive sample. According to an advantageous implementation, the tracked (or initialized) object can be shifted and rotated in order to generate a number of additional positive samples near the tracked object. A certain number of image patches more than a certain distance away from the tracked object in the current frame may be randomly selected as negative samples. At 614, the discriminant vector A is updated using gradient descent, as shown in Equations (7) and (8). At 616, the probabilistic model is updated based on the updated discriminant vector, as shown in Equation (5). At 618, The Bayesian error C(A) is calculated for the updated discriminant vector using Equation (6). Steps 614-618 are repeated until the discriminant vector A converges or the Bayesian error C(A) is less than a threshold (e.g., 0.1). Although not shown in FIG. 6, it is also possible that steps 614-618 are repeated until a maximum number of iterations is reached. At 620, when the learning converges, the updated discriminant vector and probabilistic model are stored and the tracked objects in the current frame are saved as positive training samples. Accordingly, each frame for which the algorithm is repeated adds additional positive training samples corresponding to the tracked object in that frame.

Returning to FIG. 5, at step 508, the next frame of the fluoroscopic image sequence is received. The next frame may be received directly from an image acquisition device. For example, the next frame can be received and processed in real-time during a TAVI procedure. It is also possible that the next frame is received by loading the next frame from a fluoroscopic image sequence stored in a storage or memory of a computer system. At this point, the received next frame is considered to be the current frame.

At step 510, the object is tracked in the current frame based on the adaptive discriminant model, a trained object detector, and an online appearance model using measurement fusion. The tracking of the object infers unknown object states, e.g., the catheter motion denoted as $m_t$, from an observed image sequence $Z_{1:t}$. Embodiments of the present invention formalize the parameter inference in a sequential Bayesian framework. Assuming a commonly used Markov property for tracking, the posterior probability $P(m_t|Z_{1:t-1})$ can be expressed as:

$$P(m_t|Z_{1:t-1}) = \int P(m_t|m_{t-1})P(m_{t-1}|Z_{1:t-1})dm_{t-1}$$
$$P(m_t|Z_{1:t}) \propto P(m_t|Z_{1:t-1})P(Z_t|m_t). \quad (9)$$

In Equation (9), $P(m_t|Z_{1:t-1})$ is the motion prior probability which is propagated from previous frames of the fluoroscopic image sequence. $P(m_t|m_{t-1})$ is a dynamic model. In an advantageous implementation, the dynamic probability is modeled as a Gaussian model, i.e., $P(m_t|m_{t-1}) = G(m_t; m_{t-1}, \Sigma_m)$, where G is a Gaussian distribution with the mean of $m_{t-1}$ and the covariance matrix of $\Sigma_m$. The Gaussian prior model is used as the dynamic model due to its simplicity and effectiveness of imposing smoothness constraints for 2D motions. The Gaussian dynamic model gives a greater probability to objects having a state that is close to the object tracked in the previous frame. Another component, the likelihood measurement model $P(Z_t|m_t)$, measures the likelihood of motion parameters. The tracking result for an object in a frame is the motion parameter corresponding to the maximal posterior probability:

$$\hat{m}_t = \underset{m_t}{\operatorname{argmax}} P(m_t | Z_{1:t}). \quad (10)$$

In visual tracking, the measurement model plays a critical role, as it directly relates observed images to object states to be inferred. However, it is difficult for one measurement model to handle dynamic changes of objects and cluttered background. According to an advantageous aspect of the present invention, the measurement model $P(Z_t|m_t)$ is a fusion of multiple measurement models.

Assuming that there are K measurement models for an object, i.e., $P^{(k)}(Z_t|m_t) = P(Z_t|m_t,k)$, $k=1, \ldots, K$, a Bayesian measurement fusion based on the probability marginalization can be expressed as:

$$P(Z_t | m_t) = \sum_k P(Z_t | m_t, k) P(k | m_t). \quad (11)$$

For simplicity, it can be assumed that the measurement model prior $P(k|m_t)$ does not change with object states during tracking, i.e., $P(k|m_t)=\omega_k$, and $\Sigma_k \omega_k = 1$. $\omega_k$ denotes a weight of the k-th measurement model. Therefore, an overall measurement model can be expressed as $P(Z_t|m_t)=\Sigma k \omega_k P^{(k)}(Z_t|m_t)$, and equation (9) can be re-written as:

$$P(m_t | Z_{1:t}) \propto P(m_t | Z_{1:t-1}) \sum_k \omega_k P^{(k)}(Z_t | m_t). \quad (12)$$

In an advantageous embodiment of the present invention, three types of measurement models are fused. The first is the adaptive discriminant model learned online (at step 506), as described above. The adaptive discriminant model is denoted as $P^{(1)}(Z_t|m_t)=P_A(x_{m_t})$, in equation $x_{m_t}$, as in equation (5), where x. is the data vector extracted from the observed images based on the object state $m_t$. The other two measurement models are from an offline trained object detector and an online appearance model.

In order to provide the offline learning based measurement model, an object detector can be trained offline based on a set of annotated training samples. Such a trained object detector is capable of modeling objects with large variations and also may be robust to background noise. In an advantageous implementation, a probabilistic boosting tree (PBT) can be used to train the object detector. A PBT is a tree based generalized form of AdaBoost classifiers and can effectively model a complex distribution of a class of objects. The object detector can be trained using Haar features. The output of a trained PBT classifier, denoted as $f(x)$, is a combination of outputs from a collection of learned weak classifiers $H_k(x)$ with associated weights $\alpha_k$, i.e., $f(x)=\Sigma k \alpha_k H_k(x)$. The outputs of the trained PBT object detector can be interpreted into probabilistic measurements for input image patches, as expressed in equation (13):

$$P^{(2)}(Z_t | m_t) = \frac{e^{f(x_{m_t})}}{e^{-f(x_{m_t})} + e^{f(x_{m_t})}}. \quad (13)$$

Although PBT is used, the present invention is not limited thereto. It is also possible, that other probabilistic classifiers are used as the offline learning based measurement model, for example, SVM, k-NN, and Random forest.

The online appearance based measurement is used to model individual object appearance, and to keep tracking the appearance changes of an object. Different from the offline learned measurement model, the appearance based measurement model aims to model the online appearance of an individual object, instead of the whole class of objects. Also different from the online adaptive discriminant model, the online appearance model is for the representation of the object, instead of the separation of an object from other portions of an image. In an advantageous implementation, the online appearance model takes the form of:

$$P^{(3)}(Z_t|m_t) \propto G(D(x_{m_t}); \sigma_\alpha), \quad (14)$$

where G is a one dimensional Gaussian kernel with a zero mean and a bandwidth of $\sigma_\alpha$. $D(x_{m_t})$ is a robust distance function that calculates differences between current observations $x_{m_t}$ and an appearance template $x^0$, given by:

$$D(m_t) = \sum_k c_k \rho(x_{m_t}(s_k) - x^0(s_k); \sigma_a). \quad (15)$$

In equation (15), $\{s_k\}$ is a set of pixels in the image template. Each pixel in the template is assigned a weight, $c_k$, to de-emphasize the pixels far away from the template center. The pixel weight is set as $c_k = G(-|s_k|; \sigma_t)$, where $|s_k|$ is the distance for $s_k$ to the template center, and $\sigma_t$ is set as the image template size. $\rho$ is a robust function to remove outliers:

$$\rho(y; \sigma_a) = \begin{cases} |y|, & \text{if } |y| <= 3\sigma_a \\ 3\sigma_a, & \text{if } |y| > 3\sigma_a. \end{cases} \quad (16)$$

During tracking, the template $x^0$ is updated by the tracking results to keep up with dynamic object changes. The template updating may be sensitive to image noises and prone to tracking "drifting". While it is possible to use a more sophisticated template update strategy, the present inventors have found that the simple template updating method, when fusing with other measurements, works well in a cluttered background. This further demonstrates the benefits of multiple measurement fusion.

The three measurement models $P^{(1)}(Z_t|m_t)$, $P^{(2)}(Z_t|m_t)$, and $P^{(3)}(Z_t|m_t)$ are used in equation (12) to detect the state of the object in a frame of the image sequence. For example, the measurement models can be used in equation (12) to detect image patches where the object is located in a frame. The weights of the three measurement models can be set experimentally by a user. In a possible implementation, the measurement models $P^{(1)}(Z_t|m_t)$, $P^{(2)}(Z_t|m_t)$, and $P^{(3)}(Z_t|m_t)$ can be assigned weights of $\omega_1 = 0.25$, $\omega_2 = 0.50$, and $\omega_3 = 0.25$, but the present invention is not limited thereto.

Exhaustively searching the object state space to obtain the maximal posterior probability estimation is computationally expensive. For computational efficiency, a kernel-based multi-resolution method may be used. In the multi-resolution tracking, measurements are made at a set of sample object states $m_{t,j}^s$, instead of the whole state space. In this method, $m_{t,j}^s$ are uniformly sampled in a 2D motion space. The Markov conditional independence can be assumed that the observations at sampling points $m_{t,j}^s$ are independent of the un-sampled points $m_t$, i.e., $P(Z_t|m_t, m_j^s) = P(Z_t|m_j^s)$. Therefore, the kernel-based measurement estimation can be represented as:

$$P(Z_t | m_t) = \sum_j P(Z_t | m_{t,j}^a) P(m_{t,j}^a | m_t),$$

where $P(m_{j,t}^s|m_t) = G(m_{t,j}^s; \sigma_s)$ is a Gaussian kernel with a bandwidth $\sigma_s$. The kernel-base measurement estimation can obtain smooth measurements from a set of samples, so as to reduce computations of measurements. By incrementally decreasing the sampling steps and the $\sigma_s$, coarse to fine tracking can be achieved for a frame of an image sequence.

Returning to FIG. 5, at step 512, the object tracking results for the current frame are output. For example the object tracking results may be output by displaying the objecting tracking results in the current frame of the fluoroscopic image sequence. For example, the object tracking results for the current frame can be displayed on a display of a computer system. It is also possible that the object tracking results are output by storing the output tracking results, for example in a storage or memory of a computer system.

At step 514, it is determined whether the current frame is the final frame in the fluoroscopic image sequence. If the current frame is not the final frame, the method returns to step 506. Accordingly, steps 506-512 are repeated to track the object and output the tracking results in each subsequent frame. This results in the online discriminant model being adaptively updated as the object is tracked in each frame, and the object being tracked using the adaptive discriminant model, the trained object detector measurement model, and the online appearance model in each subsequent frame. This also results the object tracking results being output for each frame in real time as the object is tracked in each frame. If the current frame is the final frame at step 514, the method proceeds to step 516. At step 516, the method ends.

Although the method of FIG. 5 illustrates an advantageous embodiment in which the object tracking results for each frame are output in real time as the object is tracked in each frame, the present invention is not limited thereto. It is also possible that the tracked results for the entire image sequence can be output together after the object is tracked in all of the frames of the fluoroscopic image sequence.

Figure 7:
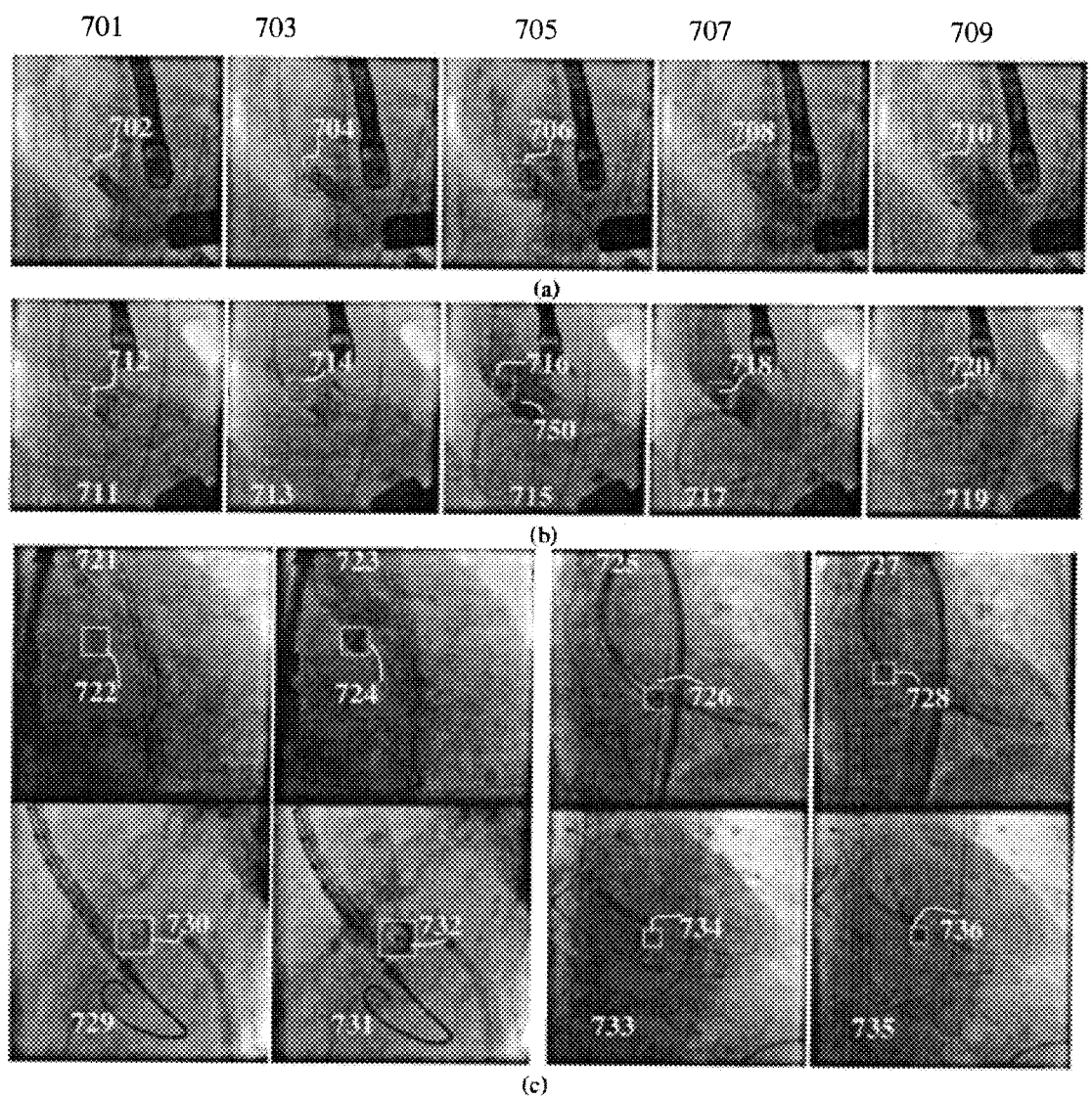
FIG. 7 illustrates exemplary pigtail catheter tracking results.

FIG. 7 illustrates exemplary pigtail catheter tracking results using the method of FIG. 5. Sequence (a) of FIG. 7 shows tracked pigtail catheter tip locations 702, 704, 706, 708, and 710 are in frames 701, 703, 705, 707, and 709, respectively. Sequence (a) shows the discriminant tracking can handle occlusion and contrast injection. Sequence (b) of FIG. 7 shows tracked pigtail catheter tip locations 712, 714, 716, 718, and 720 in frames 711, 713, 715, 717, and 719, respectively. As shown in frame 715, there is an error between the tracked pigtail catheter tip location 716 and the ground truth pigtail catheter tip location 750. Accordingly, sequence (b) shows that the robust tracking can recover from tracking error in single frames. The set of images in (c) of FIG. 7 shows additional pigtail catheter tip tracking results 722, 724, 726, 728, 730, 732, 734, and 736 in frames 721, 723, 725, 727, 729, 731, 733, and 735, respectively, of other fluoroscopic image sequences.

Figure 8:
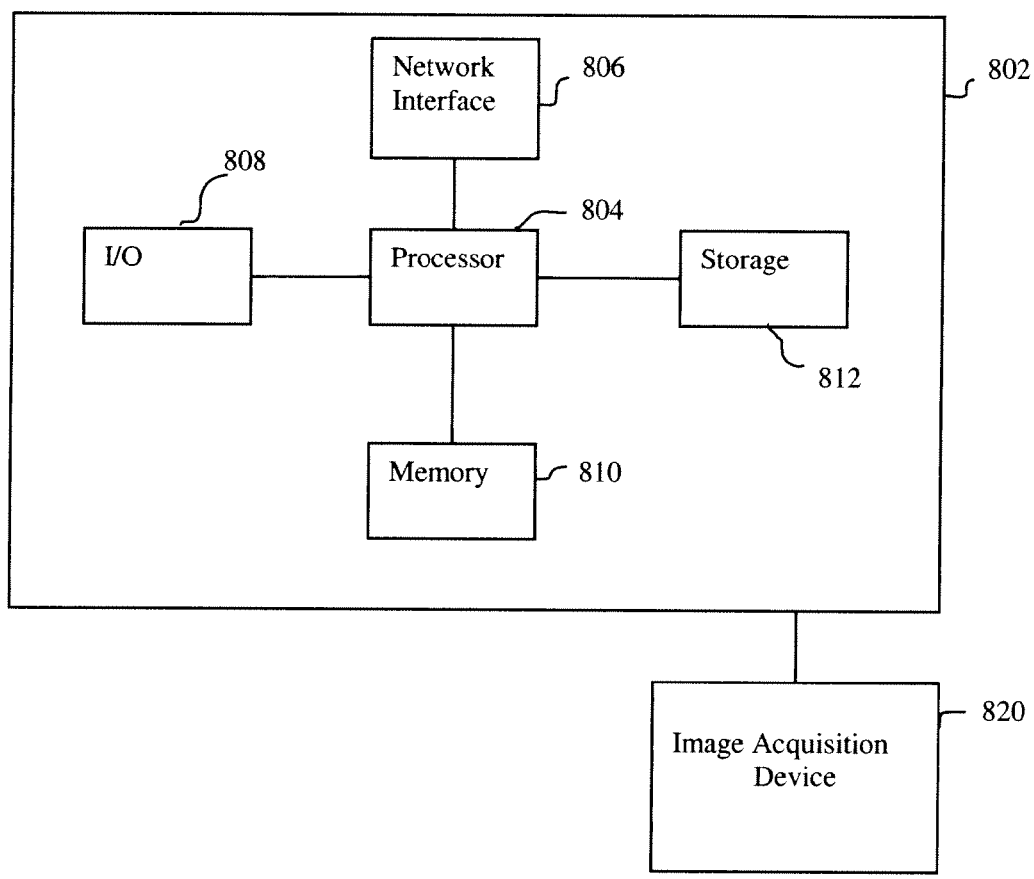
FIG. 8 is a high level block diagram of a computer capable of implementing the present invention.

The above-described methods for tracking an object, such as a pigtail catheter, in a fluoroscopic image sequence may be implemented on a computer using well-known computer processors, memory units, storage devices, computer software, and other components. A high level block diagram of such a computer is illustrated in FIG. 8. Computer 802 contains a processor 804 which controls the overall operation of the computer 802 by executing computer program instructions which define such operation. The computer program instructions may be stored in a storage device 812, or other computer readable medium (e.g., magnetic disk, CD ROM, etc.) and loaded into memory 810 when execution of the computer program instructions is desired. Thus, the steps of the methods of FIGS. 5 and 6 may be defined by the computer program instructions stored in the memory 810 and/or storage 812 and controlled by the processor 804 executing the computer program instructions. An image acquisition device 820, such as an x-ray scanning device, can be connected to the computer 802 to input images to the computer 802. It is possible to implement the image acquisition device 820 and the computer 802 as one device. It is also possible that the image acquisition device 820 and the computer 802 communicate wirelessly through a network. The computer 802 also includes one or more network interfaces 806 for communicating with other devices via a network. The computer 802 also includes other input/output devices 808 that enable user interaction with the computer 802 (e.g., display, keyboard, mouse, speakers, buttons, etc.). One skilled in the art will recognize that an implementation of an actual computer could contain other components as well, and that FIG. 8 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for tracking an object in a sequence of fluoroscopic images, comprising:
    training an adaptive discriminant model online based on a tracked object in at least one previous frame of the fluoroscopic image sequence; and
    tracking the object in a current frame of the fluoroscopic image sequence based at least on the adaptive discriminant model trained online, wherein tracking the object in a current frame of the fluoroscopic image sequence based at least on the adaptive discriminant model trained online comprises:
        tracking the object in the current frame using an overall measurement model that is a fusion of the adaptive discriminant model trained online, an object detection model trained offline, and an online appearance model.

2. The method of claim 1, wherein the step of training an adaptive discriminant model online based on a tracked object in at least one previous frame of the fluoroscopic image sequence comprises:
    extracting positive samples from the tracked object in the at least one previous frame and negative samples away from the tracked object in the at least one previous frame;
    updating a linear discriminant vector based on the extracted positive samples and negative samples using a gradient descent method to reduce a Bayesian error; and
    updating a probabilistic model based on the updated linear discriminant vector.

3. The method of claim 2, wherein the step of training an adaptive discriminant model online based on a tracked object in at least one previous frame of the fluoroscopic image sequence further comprises:
    repeating the steps of updating the linear discriminant vector and updating the probabilistic model until the linear discriminant vector converges.

4. The method of claim 2, wherein an initial linear discriminant vector is trained offline based on annotated training data.

5. The method of claim 4, wherein the initial linear discriminant vector is trained offline using principal component analysis (PCA) to reduce the dimensionality of the training data and Fisher discriminant analysis (FDA) applied to principal components result from the PCA to learn the initial discriminant vector.

6. The method of claim 1, wherein the object detection model is trained offline based on annotated training data using a probabilistic boosting tree (PBT).

7. The method of claim 1, wherein the online appearance model calculates a probabilities for image patches in the current frame based on differences between the image patches and an appearance template trained online from the tracked object in the at least one previous frame.

8. The method of claim 1, wherein the step of tracking the object in the current frame using an overall measurement model that is a fusion of the adaptive discriminant model trained online, an object detection model trained offline, and an online appearance model comprises:
tracking the object in the current frame based on a motion prior probability which is propagated from the at least one previous frame and the overall measurement model.

9. The method of claim 1, wherein the step of tracking the object in a current frame of the fluoroscopic image sequence based at least on the adaptive discriminant model trained online comprises:
detecting motion parameters $m_t$ in the object in the current frame t to maximize a posterior probability $P(m_t|Z_{1:t})$:

$$P(m_t|Z_{1:t}) \propto P(m_t|Z_{1:t-1}) \sum_{k=1}^{3} \omega_k P^{(k)}(Z_t|m_t),$$

where $Z_i$ is observed image data of frame i, $P(m_t|Z_{1:t-1})$ is a motion prior probability propagated from the at least one previous frame, $P^{(1)}(Z_t|m_t)$ is the adaptive discriminant model trained online, $P^{(2)}(Z_t|m_t)$ is a probabilistic measurement from an object detector trained offline, and $P^{(3)}(Z_t|m_t)$ is an online appearance model.

10. The method of claim 1, wherein the object is a pigtail catheter tip.

11. An apparatus for tracking an object in a sequence of fluoroscopic images, comprising:
means for training an adaptive discriminant model online based on a tracked object in at least one previous frame of the fluoroscopic image sequence; and
means for tracking the object in a current frame of the fluoroscopic image sequence based at least on the adaptive discriminant model trained online, comprising:
means for tracking the object in the current frame using an overall measurement model that is a fusion of the adaptive discriminant model trained online, an object detection model trained offline, and an online appearance model.

12. The apparatus of claim 11, wherein the means for training an adaptive discriminant model online based on a tracked object in at least one previous frame of the fluoroscopic image sequence comprises:
means for extracting positive samples from the tracked object in the at least one previous frame and negative samples away from the tracked object in the at least one previous frame;
means for updating a linear discriminant vector based on the extracted positive samples and negative samples using a gradient descent method to reduce a Bayesian error; and
means for updating a probabilistic model based on the updated linear discriminant vector.

13. The apparatus of claim 12, further comprising:
means for training an initial linear discriminant vector offline based on annotated training data.

14. The apparatus of claim 11, wherein the object detection model is trained offline based on annotated training data using a probabilistic boosting tree (PBT).

15. The apparatus of claim 11, wherein the online appearance model calculates a probabilities for image patches in the current frame based on differences between the image patches and an appearance template trained online from the tracked object in the at least one previous frame.

16. The apparatus of claim 11, wherein the means for tracking the object in the current frame using an overall measurement model that is a fusion of the adaptive discriminant model trained online, an object detection model trained offline, and an online appearance model comprises:
means for tracking the object in the current frame based on a motion prior probability which is propagated from the at least one previous frame and the overall measurement model.

17. The apparatus of claim 11, wherein the object is a pigtail catheter tip.

18. A non-transitory computer readable medium encoded with computer executable instructions for tracking an object in a sequence of fluoroscopic images, the computer executable instructions defining a method comprising:
training an adaptive discriminant model online based on a tracked object in at least one previous frame of the fluoroscopic image sequence; and
tracking the object in a current frame of the fluoroscopic image sequence based at least on the adaptive discriminant model trained online, wherein tracking the object in a current frame of the fluoroscopic image sequence based at least on the adaptive discriminant model trained online comprises:
tracking the object in the current frame using an overall measurement model that is a fusion of the adaptive discriminant model trained online, an object detection model trained offline, and an online appearance model.

19. The non-transitory computer readable medium of claim 18, wherein the step of training an adaptive discriminant model online based on a tracked object in at least one previous frame of the fluoroscopic image sequence comprises:
extracting positive samples from the tracked object in the at least one previous frame and negative samples away from the tracked object in the at least one previous frame;
updating a linear discriminant vector based on the extracted positive samples and negative samples using a gradient descent method to reduce a Bayesian error; and
updating a probabilistic model based on the updated linear discriminant vector.

20. The non-transitory computer readable medium of claim 19, wherein the step of training an adaptive discriminant model online based on a tracked object in at least one previous frame of the fluoroscopic image sequence further comprises:
repeating the steps of updating the linear discriminant vector and updating the probabilistic model until the linear discriminant vector converges.

21. The non-transitory computer readable medium of claim 19, wherein an initial linear discriminant vector is trained offline based on annotated training data.

22. The non-transitory computer readable medium of claim 18, wherein the object detection model is trained offline based on annotated training data using a probabilistic boosting tree (PBT).

23. The non-transitory computer readable medium of claim 18, wherein the online appearance model calculates a probabilities for image patches in the current frame based on differences between the image patches and an appearance template trained online from the tracked object in the at least one previous frame.

24. The non-transitory computer readable medium of claim 18, wherein the step of tracking the object in the current frame using an overall measurement model that is a fusion of the adaptive discriminant model trained online, an object detection model trained offline, and an online appearance model comprises:
   tracking the object in the current frame based on a motion prior probability which is propagated from the at least one previous frame and the overall measurement model.

25. The non-transitory computer readable medium of claim 18, wherein the step of tracking the object in a current frame of the fluoroscopic image sequence based at least on the adaptive discriminant model trained online comprises:
   detecting motion parameters $m_t$ in the object in the current frame t to maximize a posterior probability $P(m_t|Z_{1:t})$:

$$P(m_t | Z_{1:t}) \propto P(m_t | Z_{1:t-1}) \sum_{k=1}^{3} \omega_k P^{(k)}(Z_t | m_t),$$

where $Z_i$ is observed image data of frame i, $P(m_t|Z_{1:t-1})$ is a motion prior probability propagated from the at least one previous frame, $P^{(1)}(Z_t|m_t)$ is the adaptive discriminant model trained online, $P^{(2)}(Z_t|m_t)$ is a probabilistic measurement from an object detector trained offline, and $P^{(3)}(Z_t|m_t)$ is an online appearance model.

26. The non-transitory computer readable medium of claim 18, wherein the object is a pigtail catheter tip.

\* \* \* \* \*